United States Patent [19]

Zank et al.

[11] Patent Number: 5,252,684
[45] Date of Patent: Oct. 12, 1993

[54] BORAZINE DERIVATIZED HYDRIDOPOLYSILAZANE POLYMERS

[76] Inventors: Gregg A. Zank, 500 Sylvan La., Midland, Mich. 48640; Larry G. Sneddon, 813 Briarwood Rd., Newtown Square, Pa. 19073; Kai Su, 4315 Larchwood Ave., Third Floor, Philadelphia, Pa. 19104

[21] Appl. No.: 970,505

[22] Filed: Nov. 2, 1992

[51] Int. Cl.$^5$ ............................................. C08F 283/00
[52] U.S. Cl. ......................................... 525/474; 528/7
[58] Field of Search ............................ 528/7; 525/474

[56] References Cited

U.S. PATENT DOCUMENTS

| | | |
|---|---|---|
| 4,540,803 | 9/1985 | Cannady . |
| 4,604,367 | 8/1986 | Takamizawa et al. . |
| 4,910,173 | 3/1990 | Niebylski . |
| 5,030,744 | 7/1991 | Funayama et al. . |

FOREIGN PATENT DOCUMENTS 0364323  4/1990  European Pat. Off. .

OTHER PUBLICATIONS

D. Seyferth et al., J. Am. Ceram. Soc., 73 [7], 2131-33, (1990), "Borasilazane Polymeric Precursors for Borosilicon Nitride".
D. Seyferth et al., "Silicon Ceramics with a Dash of Boron", Dept. of Chem., Massachusetts Institute of Technology, pp. 15-27.

*Primary Examiner*—Melvyn I. Marquis
*Attorney, Agent, or Firm*—Roger E. Gobrogge

[57] ABSTRACT

The present invention relates to a method of preparing borazine modified hydridopolysilazane polymers. The method comprises reacting a hydridopolysilazane polymer with a material comprising at least one borazine ring for a time sufficient to produce the desired polymer. This invention also relates to the novel polymers produced by the above method.

15 Claims, No Drawings

BORAZINE DERIVATIZED HYDRIDOPOLYSILAZANE POLYMERS

BACKGROUND OF THE INVENTION

The present invention relates to a method of preparing borazine modified hydridopolysilazane polymers. The method comprises reacting a hydridopolysilazane polymer with a material comprising at least one borazine ring for a time sufficient to produce the desired polymer. This invention also relates to the novel polymers produced by the above method.

A variety of polysilazane oligomer, cyclics, resins and linear polymers are known in the art. Generally, such polymers are characterized as having backbones with alternating silicon and nitrogen atoms. Cannady, in U.S. Pat. No. 4,540,803, issued Sep. 10, 1985, described a novel class of silazane polymers (hydridopolysilazanes) having a three-dimensional structure formed by the presence of HSi(NH)$_3$ and R$_3$SiNH groups. This unique structure afforded such polymers physical properties which are desirable in the formation of various ceramic materials.

Boron-compound-modified polysilazane polymers and various methods for their preparation are also known in the art. For instance, U.S. Pat. No. 5,030,744 granted to Funayama et al. describes the formation of boron-compound-modified polysilazanes by reacting a polysilazane having repeating units comprising:

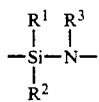

with a boron compound (including a borazine). The polysilazanes described in this reference, however, differ from those claimed in the present invention in that those of the reference are primarily linear or cyclic. In contrast, polysilazanes of the present application are the highly branched, three-dimensional polymers of Cannady, supra. Moreover, the boron compound is used in the reference to crosslink the polysilazanes and thereby increase the molecular weight. On the other hand, the borazine is used in the present invention both to react with the N-Si bond and thus cleave the hydridopolysilazane polymer thereby reducing the molecular weight of the hydridopolysilazane starting material or to react with either the N-H bond or the terminal N-trimethylsilyl bond to add a borazine group to the hydridopolysilazane polymer and thereby essentially maintain the molecular weight of the hydridopolysilazane starting material.

Likewise, European Patent No. 364,323 granted to Ardaud et al., U.S. Pat. No. 4,910,173 granted to Niebylski, and Seyferth et al., J. Am. Ceram. Soc. 73, 2131-2133 (1990), describe various other methods of forming boron-compound-modified polysilazane polymers. These references teach reacting a polysilazane with a trihalogen borane, a boroxine, or a borane, respectively. As with the Funayama patent described above, however, these references do not describe the polysilazanes of the present invention. In addition, neither Ardaud et al. nor Niebylski taught that borazine can be used in the reactions described therein.

Seyferth et al. describe the preparation of a silazane precursor for BN/Si$_3$N$_4$ ceramic materials wherein a diborane is reacted with a mixture of cyclosilazanes obtained by ammonolysis of methyldichlorosilane to form an intermediate, which Seyferth proposed to be silyl-substituted borazine, which in turn is heated and thus polymerized. The present invention can be distinguished from this reference because there is a distinct difference in structure between the one-dimensional cyclosilazanes used therein and the three-dimensional hydridopolysilazanes used in the present invention. Furthermore, Seyferth et al. in Front. Organosilicon Chem., Proc. Int. Symp. Organosilicon Chem., 9th, Meeting Date 1990, 15-27, a later investigation on the same topic, only taught that borazine incorporation retards the crystallization of the Si$_3$N$_4$ ceramic phase after pyrolysis, while the present invention claims that crystallization of both Si$_3$N$_4$ and SiC ceramic phases are retarded in the borazine modified hydridopolysilazane after pyrolysis under a purge of argon to greater 1600° C.

Zank, in U.S. patent application Ser. No 07/810,972, filed Dec. 20, 1991, now U.S. Pat No. 5,169,908 describes a method of preparing boron-compound-modified hydridopolysilazane polymer by reacting borane with the hydridopolysilazane polymer. However, this reference did not teach the reactivity of a cyclic borazine with the highly branched and three-dimensional polysilazane polymer. In addition, the borane modified the hydridopolysilazane precursor by adding a BH$_2$ group to the hydridopolysilazane polymer, whereas the borazine in the present invention both reacts to cleave the hydridopolysilazane precursor and to add the borazinyl group to the polymer.

Therefore, what has not been described in the prior art is the use of borazines to modify the specific polymers claimed herein. The present inventors have discovered that such derivatized polymers have the same or lower molecular weight than the polysilazane precursors and have properties superior to those known in the art.

SUMMARY OF THE INVENTION

The present invention describes a method of forming borazine modified hydridopolysilazane polymers. The method comprises reacting a material comprising at least one borazine ring having a hydrogen atom attached to at least one boron or nitrogen thereof, with a R$^3$SiNH- and HSi(NH)$_3$-containing polysilazane polymer for a time sufficient to form the borazine modified hydridopolysilazane polymer at a temperature below about 300° C., wherein R$^3$ is independently selected from the group consisting of hydrogen radicals, phenyl radicals, vinyl radicals and alkyl radicals containing 1 to 3 carbon atoms.

The present invention also relates to the novel polymers produced by this process.

DETAILED DESCRIPTION OF THE INVENTION

The present invention is based on the discovery that borazines can be used to modify the hydridopolysilazane polymers claimed herein to form their borazine modified derivatives. Four separate mechanisms by which the borazine modification occur are proposed by the inventors and can be described as follows:

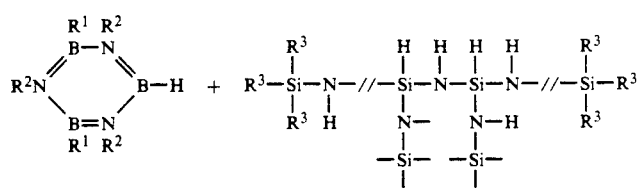
[borazine ring]  [three-dimensional hydridopolysilazane polymer]
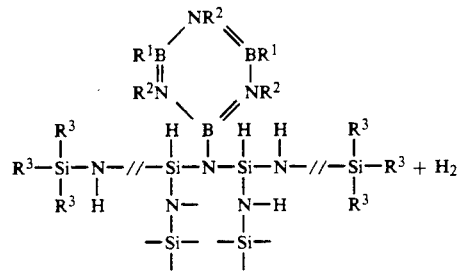
[borazine modified hydridopolysilazane polymer]
[I]
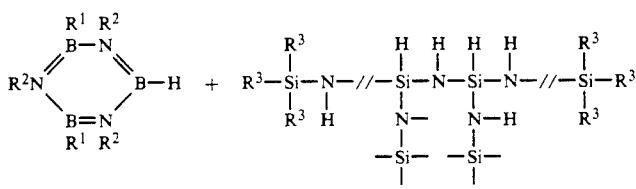
[borazine ring]  [three-dimensional hydridopolysilazane polymer]
[borazine modified hydridopolysilazane polymer]
[II]
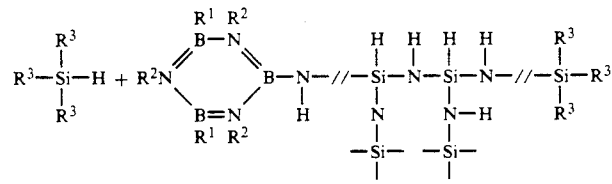
[borazine ring]  [three-dimensional hydridopolysilazane polymer]
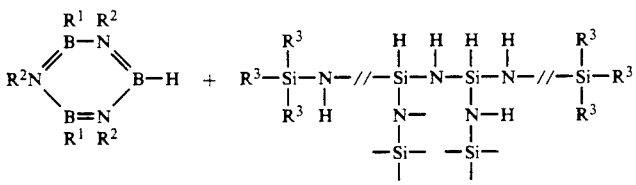
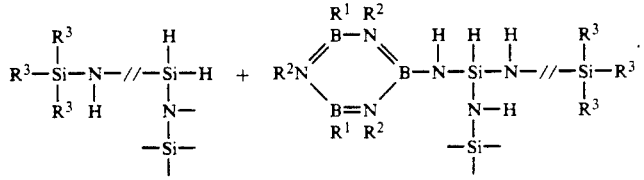
[borazine modified hydridopolysilazane polymers]
[III]

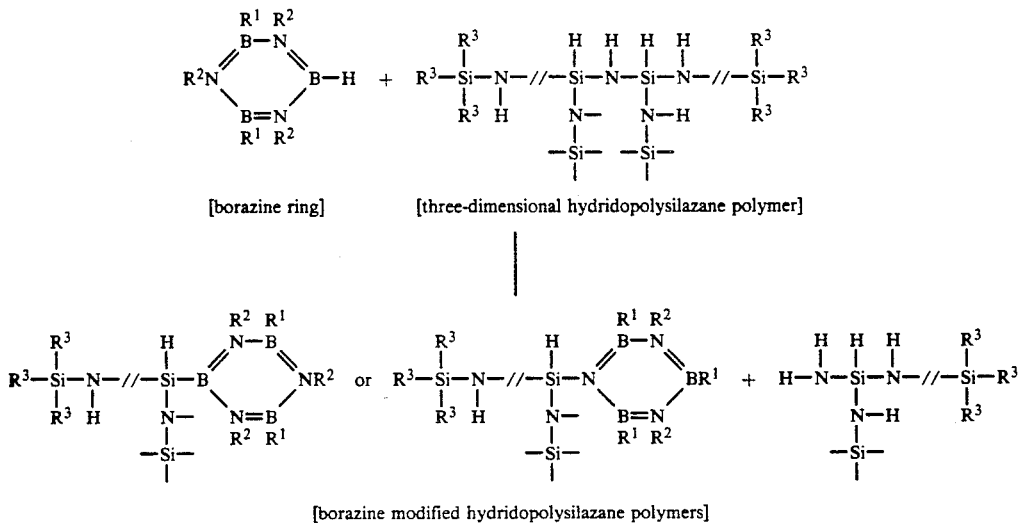

[borazine modified hydridopolysilazane polymers]

This modification reaction was unexpected since it was not known whether the highly branched polymers of the starting materials could be caused to react in the above manner (due to issues such as steric hindrance) without further polymerizing the hydridopolysilazane. Moreover, it was unexpected that this reaction would result in a decrease in molecular weight of the polymer. This result indicates that the hydridopolysilazane polymer is cleaved during the reaction as described in reaction mechanisms [III] and [IV].

The hydridopolysilazane polymers useful herein are those described in U.S. Pat. No. 4,540,803, granted to Cannady Sep. 10, 1985, and incorporated herein by reference. These polymers comprise a series of repeating units of the formula -Si-NH-Si- as described above in reaction mechanisms [I], [II], [III] and [IV]. The structure of these polymers comprises highly three-dimensional cages formed by crosslinking. These polymers are prepared by a method which comprises contacting and reacting in an inert essentially anhydrous atmosphere, trichlorosilane with a disilazane at a temperature in the range of 25° to 300° C. while distilling volatile byproducts.

The trichlorosilane is treated with sufficient disilazane to react with all of the chlorine in the trichlorosilane. The amount of disilazane used is at least equimolar to the trichlorosilane, based on the number of Si-N bonds of the disilazane and the chlorine content of the trichlorosilane i.e., 1.5 moles of disilazane per mole of trichlorosilane. The preferred ratio is between 2.5 to 3 moles of disilazane per mole of trichlorosilane.

The disilazane used in the Cannady invention has the formula $(R^3{}_3Si)_2NH$, where $R^3$ is independently selected from the group consisting of hydrogen radicals, phenyl radicals, vinyl radicals and alkyl radicals containing 1 to 3 carbon atoms. Thus, each $R^3$ can be, for example, hydrogen, methyl, ethyl, propyl, vinyl or phenyl. Examples of suitable disilazanes include $[(CH_3)_3Si]_2NH$, $[C_6H_5(CH_3)_2Si]_2NH$, $[(C_6H_5)_2CH_3Si]_2NH$, $[CH_2=CH(CH_3)_2Si]_2NH$, $[CH_2=CH(CH_3)C_6H_5Si]_2NH$, and $[CH_2=CH(C_6H_5)C_2H_5Si]_2NH$, An especially preferred embodiment of the Cannady invention involves the reaction of trichlorosilane with hexamethyldisilazane. The polymer produced thereby, trimethylsilyl hydridopolysilazane, has been shown to have valuable preceramic properties.

The above reactants are brought together in an inert essentially anhydrous atmosphere. By inert it is meant that the reaction is carried out under a blanket of inert gas such as argon, nitrogen or helium. What is meant by essentially anhydrous is that the reaction is preferably carried out in an absolutely anhydrous atmosphere but minute amounts of moisture can be tolerated.

When the reactants are contacted with each other an intermediate amino compound is formed. It is preferred that the reactants are brought together in such a manner to keep the initial reaction exotherm to a minimum. Upon continued heating additional amino compound is formed and, with further heating, $R_3SiCl$ is distilled from the reaction mixture and the silazane polymer formed. For best results, the rate of heating should be controlled at a rate of less than about 1° C./min. A heating rate of about 0.5° C./min or less is preferred. As the temperature of reaction is raised, more condensation takes place and branching occurs with residual $R^3{}_3Si$- that is not distilled from the mixture acting as a chain stopper. This control allows one to stop the reaction at any point to obtain almost any desired viscosity. The desired temperature range for the reaction is 25° to 300° C. with a temperature in the range of 125° to 275° C. being more preferred. The length of time that the reaction requires depends on the temperature employed and the polymer viscosity one wishes to achieve.

After the above polymer is formed, it is reacted with a material comprising at least one borazine ring to produce the desired borazine modified hydridopolysilazane polymer. The material useful herein comprises at least one borazine ring having a hydrogen atom attached to at least one nitrogen or boron thereof. Any material known in the art comprising at least one such borazine ring can be used in the present invention.

As shown in proposed reaction mechanisms [I], [II], [III] and [IV], a preferred embodiment of the invention comprises reacting the hydridopolysilazane with a material comprising at least one borazine ring of the general formula $(BR^1\text{-}NR^2)_3$ wherein at least one $R^1$ or $R^2$ is a hydrogen radical. The remaining $R^1$ and $R^2$ in said borazine ring are independently selected from the group consisting of hydrogen radicals, hydrocarbon radicals containing 1 to 20 carbon atoms, borazine substituted hydrocarbon radicals and radicals containing boron and nitrogen. The hydrocarbon radicals can be linear or cyclic groups. Thus, $R^1$ and $R^2$ can be, for example, alkyl radicals such as methyl, ethyl, propyl, isopropyl, hexyl, or octadecyl; alkenyl radicals such as vinyl, allyl or hexenyl; cycloaliphatic radicals such as cyclopentyl, cyclohexyl or cyclohexenyl; aromatic hydrocarbon radicals such as phenyl or tolyl. $R^1$ and $R^2$ can also be any polyvalent hydrocarbon radical such as methylene, dimethylene, trimethylene, or octadecamethylene.

Thus, materials comprising borazine ring useful herein can be monomers such as, for example, $(BH-NH)_3$, mono-B-methyl borazine, di-B methyl borazine, mono-N-ethyl borazine, di-N-methyl borazine, tri-N-propyl borazine, mono-N-di-B-methyl borazine, mono-B-vinyl borazine or mono-N-phenyl-di-N-methyl borazine and borazanaphthalene. Materials comprising borazine ring useful herein can also be polymers such as, for example, polyborazylene, polyvinyl borazine and organic copolymers of polyvinyl borazine. As shown in proposed reaction mechanisms [I], [II], [III] and [IV], the proposed reactive sites in the reaction are the B-H and N-H bonds. The reactivity of the material comprising borazine ring increases with the increased number of B-H and N-H bonds. Therefore, the most preferred material comprising borazine ring is $(BH-NH)_3$.

The minimum amount of the material comprising borazine ring used in the present invention is generally the desired amount of borazine incorporated in the hydridopolysilazane. An excess borazine may be used to prevent crosslinking reaction of the polymers. The amount of excess borazine used is only limited by the cost effectiveness of the process. Preferred is an amount of the material comprising borazine ring which dissolves the hydridopolysilazane reactant to form a homogenous solution.

The reaction of the hydridopolysilazane and material comprising borazine ring is generally conducted by merely mixing the reactants in a suitable reaction vessel. This reaction can also be conducted in the presence of a solvent. The solvents which may be used herein include any which acts as a solvent for the material comprising borazine ring, the hydridopolysilazane polymer and the borazine modified hydridopolysilazane polymer without adversely affecting any of the species. The solvents may be, for example, solvents not containing active N-H bonds such as ethers, alkanes, or aromatic hydrocarbons. Most preferred is a reaction conducted without solvents.

The above reactants are generally brought together in a essentially anhydrous atmosphere. What is meant by essentially anhydrous is that the reaction is preferably carried out in a absolutely anhydrous atmosphere but minute amounts of moisture can be tolerated.

The reaction of the hydridopolysilazane polymer can be conducted in the presence of a catalyst. The catalyst which can be employed in the present reaction is any catalyst used in the art to facilitate the dehydrogenation reaction between the borazine ring and the hydridopolysilazane polymer. The dehydrogenation catalyst can be, for example, platinum dibromide. The dehydrogenation catalyst can also be, for example osmium (II), rhodium (II) or ruthenium (II) metals, each containing ligands comprising phosphines and/or carbonyls.

The reaction of the hydridopolysilazane polymer is generally conducted in a reaction environment wherefrom the hydrogen byproduct is periodically removed. For example, the reaction can be conducted in a static vacuum reaction environment with a hydrogen headspace wherefrom the hydrogen byproduct is periodically removed from the reaction vessel.

In addition, the reaction can be conducted under reflux in an inert atmosphere wherefrom the hydrogen gas is periodically purged from the system with a inert gas. By inert atmosphere it is meant that the reaction is carried out under a blanket of inert gas such as argon, nitrogen or helium.

Removal of hydrogen byproduct drives the derivatization reaction forward. Thus, the frequency of hydrogen byproduct removal affects the equilibrium of derivatization reaction.

Alternatively, the reaction can be conducted in a pressure vessel as shown in Examples 1 and 2 below. Since the increase in pressure (e.g. up to 5 atm) drives the reaction forward, removal of the hydrogen byproduct may not be necessary.

The reactants can be reacted at any temperature below the boiling point of the material comprising borazine ring, unless elevated pressures are employed. Under atmospheric pressure, the reactants can be reacted at room temperature, but preferred is a slightly elevated temperature to induce the reaction. More preferred is reaction temperature below about 300 degrees Celsius. Even more preferred is a reaction temperature below about 100 degrees Celsius. The most preferred reaction temperature is between 60 and 80 degrees Celsius. The length of time that the reaction requires depends on the temperature employed and the degree of derivatization polymer one wishes to achieve. Under increased pressure, the reaction can run to completion in less time. The amount of borazine incorporated into the hydridopolysilazane polymer can also be readily controlled by the reaction time, temperature and pressure.

After the reaction is completed, the unreacted material comprising borazine ring can be removed from the reaction vessel by any means of liquid removal well known in the art. The removal can be preformed by, for example, vacuum evaporation or distillation. The unreacted material comprising borazine ring can then recycled.

The borazine modified hydridopolysilazane polymer produced by the above reaction is then merely recovered from solution. Methods such as recrystallization or simple evaporation of the solvent under heat and/or vacuum are known in the art and useful herein.

Modification of the polymers has been confirmed by $^{11}B$ NMR data which show a fairly clean derivatization, and by IR data which show the presence of B-H, B-N, and N-H stretches that were not present in the hydridopolysilazane starting material.

The process of this invention may produce polymers having molecular weights higher than, equivalent to or less than those of the starting polymers. The expected products of the above process represented by reaction mechanisms [I] and [II] above have about the same molecular weights as their hydridopolysilazane starting materials. The expected products of the above process represented by proposed reaction mechanisms [III] and [IV] have about the same or lower molecular weights than the starting materials. Resultant polymers formed by reaction mechanism [III], however, theoretically dominate over those produced by reaction mechanism [IV], since the latter is observed to require more vigorous conditions. Experimental results are consistent with the reaction involving all of these competing mechanisms.

Even though the modification reaction results in a decrease or no change in average molecular weights, the derivatized polymers have higher ceramic yield than that of the unmodified polymer and the ceramic yield of the derivatized polymers increases with increased incorporation of boron. Furthermore, the nitrogen levels in the ceramic chars (of the derivatized polymer) are higher because of B-N bond formation. Finally, XRD results show that borazine retards crystallization of hydridopolysilazanes up to pyrolysis temperatures of 1700° C., while crystallization of the SiC and $Si_3N_4$ ceramic phases occurs in the unmodified polymer at pyrolysis temperatures of about 1500° C.

The derivatized polymers of this invention are especially valuable since they are meltable and easily curable at elevated temperatures. Such curability is critical in applications such as ceramic fibers, as coatings on ceramic and carbon-carbon composites, as ceramic monoliths, and as ceramic matrix composites.

The following non-limiting examples are provided so that one skilled in the art may more readily understand the invention.

In the following Examples, hydridopolysilazane samples of the general formula $(HSi)_{0.33}(Me_3Si)_{0.17}(NH)_{0.33}N_{0.17}$ were obtained from Dow Corning Corp. (Midland, Mich.). Borazine of the formula $(BHNH)_3$, purchased from Callery Chemical Co., was purified by refraction through $-45°$, $-78°$ and $-196°$ trap series, with only the material collected at $-78°$ used.

Elemental analyses of carbon, hydrogen and nitrogen for both the polymers and the ceramics were performed on a Control Equipment Corporation 240-XA Elemental Analyzer. Oxygen analyses were done on a Leco Oxygen Analyzer equipped with an Oxygen Determinator 316 (Model 783700) and an Electrode Furnace EFIOO. Silicon and boron compositions were determined by a fusion technique which consisted of converting the material to soluble forms of silicon and boron followed by analyzing the solute for total silicon or boron by atomic absorption spectrometry.

X-ray diffraction (XRD) characterization was performed on a Norelco Philips vertical goniometer (Type 42271/0) fitted with a closed sample chamber, sample spinner, graphite monochromator, scintillation counter, and a long fine focus copper target tube.

Gel permeation chromatography (GPC) data (i.e. molecular weight distribution averages) were obtained on a GPC (Waters Inc.) equipped with a model 600E systems controller, model 490 ultraviolet absorbance (UV) and model 410 differential refractometer detectors interfaced to a Digital Professional 380 computer employing EXPERT software (Waters Inc.). All values were relative to polystyrene standards.

Diffuse-reflectance IR spectra were obtained on a Perkin-Elmer 7770 Fourier transform spectrophotometer equipped with the appropriate diffuse-reflectance attachment. $^{11}B$ NMR spectra at 64.2 MHz were obtained on a Bruker AF 200 spectrometer equipped with the appropriate decoupling accessories. All $^{11}B$ shifts were referenced to $BF_3\text{-}O(C_2H_5)_2$(0.0 ppm) with a negative sign indicating an upfield shift. All synthetic manipulations were carried out by using standard high vacuum or inert-atmosphere techniques.

EXAMPLES 1 AND 2

A sample of hydridopolysilazane was charged into a 88 mL Fisher pressure reaction vessel and the vessel was evacuated. The purified borazine was vacuum distilled into the reactor vessel, which was sealed and brought to room temperature. The amounts of hydridopolysilazane (HPZ (g)) and borazine (borazine (g)) used for each example are detailed in Table 1. The hydridopolysilazane gradually dissolved to form a clear solution. The mixture was then heated in an oil bath and maintained at 73° C. As shown in Table 1 (time (h)), the reactant mixture which produced borazine modified polymer (1) was heated in excess borazine for 7.0 hours, while the mixture which produced borazine modified polymer (2) was heated for 17.5 hours. The borazine modified polymers were isolated as white solids after vacuum evaporation of excess borazine from the reaction vessel. The product yield for each Example is listed in Table 1 (Yield(g)).

Elemental analyses were performed on the precursor polymer (HPZ) and the borazine modified polymers (1) and (2). As shown in Table 1, more borazine is incorporated into the hydridopolysilazane polymer when the reaction time is increased at a constant temperature. GPC data (i.e.: molecular weight distribution averages) of the starting polymer (HPZ) and modified polymer (1) and polymer (2) were also obtained.

IR spectra for polymers (1) and (2) show absorptions characteristic of the brazinyl BH (2510 cm$^{-1}$) and NH (3450 cm$^{-1}$), polymer NH (3380 cm$^{-1}$), SiH at (2160 cm$^{-1}$) and saturated CH (2900–3000 cm$^{-1}$) with the relative intensities of these absorptions changing according to the polymer composition. With increasing borazine content, the backbone NH, SiH and CH absorptions decrease, while the borazine BH and NH absorptions increase. The $^{11}B$ decoupled proton NMR spectra of both reactant and product samples show broad resonances centered at 5.10 ppm (NH), 4.60 ppm (BH), and a very strong resonance at 0.2 ppm (saturated C-H attached to Si) with the relative intensities characteristic of their borazine and silazane compositions. $^{11}B$ NMR spectrum for polymer (1) is composed of a singlet at 25.8 ppm and a doublet at 31.0 ppm ($J_{BH}$=112 Hz) in a 1:2 integrated ratio, indicating the borazine unit is connected to the hydridopolysilazane through one of the three boron atoms in the borazine ring. The chemical shifts are characteristic of those observed for substituted borazines suggesting no ring-opening reaction has occurred. The $^{11}B$ NMR spectra for modified polymer (2) contained similar features as polymer (1). However, the resonances in the higher borazine content polymer (2) were broadened.

Other characteristics of the polymers are summarized in Table 2.

TABLE 1

Summary of Reaction Conditions and Modified Polymer Yield and Compositions

| polymer | HPZ (g) | Borazine (g) | T (°C.) | time (h) | Yield (g) | Polymer Composition |
|---------|---------|--------------|---------|----------|-----------|---------------------|
| HPZ | — | — | — | — | — | $Si_{1.0}N_{1.04}C_{1.16}H_{4.69}$ |

TABLE 1-continued

Summary of Reaction Conditions
and Modified Polymer Yield and Compositions

| polymer | HPZ (g) | Borazine (g) | T (°C.) | time (h) | Yield (g) | Polymer Composition |
|---|---|---|---|---|---|---|
| (1) | 1.52 | 3.24 | 73 | 7.0 | 1.56 | $Si_{1.0}B_{0.32}N_{1.22}C_{1.02}H_{4.67}$ |
| (2) | 1.51 | 3.15 | 73 | 17.5 | 2.28 | $Si_{1.0}B_{1.68}N_{2.61}C_{1.04}H_{6.25}$ |

TABLE 2

Characterization of the Hydridopolysilazane Precursor
and Borazine Modified Products

| | elemental analyses (wt %) | | | | | GPC | |
|---|---|---|---|---|---|---|---|
| polymer | % C | % H | % N | % Si | % B | Mn | Mw |
| HPZ | 21.84 | 7.42 | 23.06 | 44.3 | — | 2214 | 11,438 |
| (1) | 18.69 | 7.12 | 25.97 | 42.7 | 5.3 | 1483 | 6,729 |
| (2) | 11.96 | 6.00 | 35.15 | 26.9 | 17.42 | 783 | 4,322 |

EXAMPLE 3

26 g of hydridopolysilazane was charged into a 500 mL round bottom flask fitted with a vacuum stopcock and the flask was evacuated. 21.68 g of purified borazine was vacuum distilled into the reactor vessel, which was sealed and brought to room temperature. The polysilazane gradually dissolved to form a clear solution. The mixture was then heated in an oil bath and maintained at 73° C. The mixture which produced borazine modified polymer was heated in excess borazine for 2.2 hours. The vessel was degassed every hour. 26.8 g of borazine modified polymers were isolated as white solids after vacuum evaporation of excess borazine from the reaction vessel. Elemental analyses were performed on the precursor polymer (HPZ) and the borazine modified polymer (3).

GPC data (i.e.: molecular weight distribution averages) of polymer (3) were obtained. IR spectra for modified polymer (3) showed similar absorption characteristics as modified polymers (1) and (2). The $^{11}B$ NMR spectra for modified polymer (3) contained similar features as modified polymers (1) and (2); however, the resonances in the higher borazine content polymers (1) and (2) were broader than those of polymer (3).

TABLE 3

Characterization of the Polysilazane Precursor
and the Boron Modified Polymer Product
after 2.2 hours of reaction at 73° C.

| | elemental analyses (wt %) | | | | | | GPC | |
|---|---|---|---|---|---|---|---|---|
| polymer | % C | % H | % N | % Si | % B | formulation | Mn | Mw |
| HPZ | 21.8 | 7.4 | 23.1 | 44.3 | — | $Si_{1.0}N_{1.04}C_{1.16}H_{4.09}$ | 2,214 | 11,438 |
| (3) | 2.2 | 7.4 | 24.1 | 42.8 | 2.2 | $Si_{1.0}B_{0.13}N_{1.13}C_{1.17}H_{4.84}$ | 1,6499,873 | |

As shown in Table 3. in 2.2 hours, only 2.2 wt % boron was incorporated into polymer (3), drastically less than the amount of boron incorporated in polymer (1) (5.3 wt %) and polymer (2) (17.42 wt %), when the reaction was allowed to proceed for much longer times, 7 and 17.5 hours, respectively.

EXAMPLES 4 THROUGH 6

Investigation of the ceramic conversions of the modified polymers from Examples 1, 2 and 3 were performed by converting the polymers to ceramic chars. An aliquot of the resin was weighed into a graphite crucible which was then transferred into an Astro graphite furnace equipped with Eurotherm temperature controllers. A type K thermocouple was used to monitor temperatures below 900° C. and an Ircon Modeline Plus optical pyrometer for temperatures above 900° C. The furnace was then evacuated to <20 torr and backfilled with argon. Under a purge of argon, the sample was heated to a temperature of 1400° C. at a rate of 10° C. per minute and held at that temperature for one hour. The sample was then cooled to room temperature. The resulting ceramic chars were ground for elemental analysis and x-ray diffraction (XRD) characterization, employing a mortar and pestle molded of finely powdered synthetic sapphire.

Table 4 summarizes the ceramic yield, the compositions, and the XRD results for the ceramics derived from the precursor polymer (HPZ) and the borazine modified polymers (1), (2) and (3).

TABLE 4

Ceramic Yield, Elemental and XRD Analyses of
the Polysilazane Precursor and Borazine Modified Product
after pyrolysis to 1400° C.

| | | ceramic | elemental analysis (wt %) | | | | |
|---|---|---|---|---|---|---|---|
| Example # | polymer | yield | % C | % N | % Si | % B | XRD |
| — | HPZ | 56.97% | 11.1 | 28.2 | 59.9 | — | beta-SiC and alpha $Si_3N_4$ |
| 4 | (1) | 68.31% | 9.69 | 32.66 | 52.3 | 4.4 | amorphous |
| 5 | (2) | 76.5% | 7.39 | 41.2 | 33.6 | 17.1 | amorphous |
| 6 | (3) | 70% | 10.5 | 29.9 | 53.4 | 2.4 | amorphous |

As shown in Table 4 above, the ceramic chars of boron modified polymers (1), (2) and (3) are predominantly amorphous after pyrolysis to 1400° C. Moreover, higher ceramic yield results when boron is incorporated into the hydrdopolysilazane polymer.

EXAMPLES 7 THROUGH 11

Investigation to determine the temperatures to which these borazine modified hydridopolysilazane materials can retain nitrogen and remain amorphous was performed. Aliquots of the precursor polymer (HPZ) and modified polymer (3) were weighed into a graphite crucible, which was transferred into an Astro graphite furnace equipped with Eurotherm temperature controllers. A type K thermocouple was used to monitor temperatures below 900° C. and an Ircon Modeline Plus optical pyrometer for temperatures above 900° C. The furnace was then evacuated to <20 torr and backfilled with argon. Under a purge of argon, the sample was heated to temperatures of 1400° C. (Ex. 7), 1500° C. (Ex.8), 1600° C. (Ex. 9), 1700° C. (Ex. 10) and 1800° C. (Ex. 11), at a rate of 10° C. per minute. In each example, the sample was held at the respective pyrolysis temperature for one hour. The sample was then cooled to room temperature. The resulting ceramic chars were ground for elemental analysis and XRD characterization, employing a mortar and pestle molded of finely powdered synthetic sapphire.

Table 5 below summarizes the percent ceramic yields (% ceramic yield), composition of nitrogen (wt %N) in weight percent and XRD results for the ceramics derived from the precursor polymer (HPZ polymer) and the borazine modified polymer (3).

white solid that was obtained upon solvent evaporation was performed on a GPC. Table 6 shows that there was no decrease and only a modest increase in molecular weight in the heated polymer (heated) when compared to the starting hydridopolysilazane polymer (HPZ).

TABLE 6

Molecular Weight Distribution Averages of unheated versus heated starting hydridopolysilazane polymer

| polymer | GPC | |
|---|---|---|
| | Mn | Mw |
| HPZ | 2,214 | 11,438 |
| heated | 1,365 | 12,388 |

We claim:

1. A method of forming a borazine modified hydridopolysilazane polymer comprising:
reacting a material comprising at least one borazine ring having a hydrogen atom attached to at least one nitrogen or boron thereof, with a three dimensional hydridopolysilazane polymer having

TABLE 5

Ceramic Yield, Nitrogen Composition and XRD of Polysilazane Precursor and Borazine Modified Product

| | | HPZ polymer | | | modified polymer (3) | | |
|---|---|---|---|---|---|---|---|
| ex. # | pyrolysis temperature | ceramic yield | wt % N | XRD | ceramic yield | wt % N | XRD |
| 7 | 1400° C. | 62.3% | 29.3 | major amorphous minor alpha-Si3N4 beta-SiC | 68.8% | 29.9 | major amorphous trace alpha-Si3N4 beta-SiC |
| 8 | 1500° C. | 61.3% | 28.9 | major alpha-Si3N4 minor amorphous beta-SiC | 69.9% | 28.8 | major amorphous minor alpha-Si3N4 |
| 9 | 1600° C. | 55.5% | 23.8 | major beta-SiC alpha-Si3N4 minor alpha-SiC | 62.9% | 28.6 | major amorphous minor alpha-Si3N4 beta-SiC |
| 10 | 1700° C. | 44.1% | 4.11 | major beta-SiC | 59.1% | 25.1 | major alpha-Si3N4 beta-SiC trace amorphous |
| 11 | 1800° C. | 42.4% | 1.00 | 100% beta-SiC | 51.1% | 15.3 | major beta-SiC minor beta-Si3N4, Si |

Table 5 shows minimal nitrogen loss for the boron containing ceramics throughout the pyrolysis region studied. In addition, while the unmodified hydridopolysilazane achieved crystallization at 1500° C., retardation of crystallization is observed up to 1700° C. in the boron containing ceramics. These results suggest that ceramic fibers made from borazine modified hydridopolysilazane polymers have more thermal stability than those made from the unmodified hydridopolysilazane polymers. Moreover, the thermal stability of the borazine modified hydridopolysilazane polymers correlates directly with their nitrogen level.

COMPARISON EXAMPLE

A control experiment to determine any thermally induced molecular weight changes in the starting hydridopolysilazane polymer was carried out by heating 0.53 g of hydridopolysilazane dissolved in 6.0 g benzene at 70° C. for 30 hours. Molecular weight study of the $R^3$SiNH- and HSi(NH)$_3$ units at a temperature below about 300° C. for a time sufficient to form the borazine modified hydridopolysilazane polymer, wherein $R^3$ are independently selected from the group consisting of hydrogen radicals, phenyl radicals, vinyl radicals and alkyl radicals containing 1 to 3 carbon atoms.

2. The method of claim 1 wherein the borazine ring has the general formula (BR$^1$-NR$^2$)$_3$, wherein at least one $R^1$ or $R^2$ is a hydrogen radical, the remaining $R^1$ and $R^2$ radicals are independently selected from the group consisting of hydrogen radicals, hydrocarbon radicals containing 1 to 20 carbon atoms, borazine substituted hydrocarbon radicals and radicals containing boron and nitrogen.

3. The method of claim 2 wherein the material comprising at least one borazine ring is selected from the group consisting of (BH-NH)$_3$, borazanaphthalene, polyborazylene and polyvinyl borazine.

4. The method of claim 1 wherein each $R^3$ is a methyl radical.

5. The method of claim 1 wherein the reaction temperature is in the range of 60° to 80° C.

6. The method of claim 1 wherein the reaction of the material comprising at least one borazine ring with the three dimensional hydridopolysilazane polymer having $R^3$SiNH- and HSi(NH)$_3$ units is conducted in a static vacuum system with a hydrogen headspace from which the byproduct hydrogen gas is periodically removed.

7. The method of claim 1 wherein the reaction of the material comprising at least one borazine ring with the three dimensional hydridopolysilazane polymer having $R^3$SiNH- and HSi(NH)$_3$ units is conducted under reflux in an inert atmosphere wherefrom the hydrogen gas is periodically purged with a inert gas.

8. The method of claim 1 wherein the reaction of the material comprising at least one borazine ring with the three dimensional hydridopolysilazane polymer having $R^3$SiNH- and HSi(NH)$_3$ units is conducted under elevated pressure.

9. The method of claim 1 wherein the reaction of the material comprising at least one borazine ring with the three dimensional hydridopolysilazane polymer having $R^3$SiNH- and HSi(NH)$_3$ units is conducted in the presence of a catalyst.

10. The method of claim 1 wherein the reaction of the material comprising at least one borazine ring with the three dimensional hydridopolysilazane polymer having $R^3$SiNH- and HSi(NH)$_3$ units is conducted in an essentially anhydrous atmosphere.

11. The method of claim 1 wherein the reaction of the material comprising at least one borazine ring with the three dimensional hydridopolysilazane polymer having $R^3$SiNH- and HSi(NH)$_3$ units is conducted in a solvent selected from the group consisting of alkanes, ethers, and aromatic hydrocarbons.

12. The borazine modified hydridopolysilazane polymers produced by the process of claim 1.

13. The borazine modified hydridopolysilazane polymers produced by the process of claim 2.

14. The borazine modified hydridopolysilazane polymers produced by the process of claim 3.

15. The borazine modified hydridopolysilazane polymers produced by the process of claim 4.

* * * * *